US009301986B2

(12) United States Patent
Misawa et al.

(10) Patent No.: US 9,301,986 B2
(45) Date of Patent: Apr. 5, 2016

(54) PPAR ACTIVATOR

(75) Inventors: Koichi Misawa, Utsunomiya (JP);
Hirofumi Takigawa, Oyama (JP);
Takatoshi Murase, Haga-gun (JP)

(73) Assignee: Kao Corporation, Tokyo (JP)

( * ) Notice: Subject to any disclaimer, the term of this patent is extended or adjusted under 35 U.S.C. 154(b) by 101 days.

(21) Appl. No.: 14/001,017

(22) PCT Filed: Feb. 21, 2012

(86) PCT No.: PCT/JP2012/054028
§ 371 (c)(1),
(2), (4) Date: Aug. 22, 2013

(87) PCT Pub. No.: WO2012/115064
PCT Pub. Date: Aug. 30, 2012

(65) Prior Publication Data
US 2014/0023735 A1   Jan. 23, 2014

(30) Foreign Application Priority Data
Feb. 22, 2011   (JP) ................. 2011-035341

(51) Int. Cl.
*A61K 36/48*   (2006.01)
*A61K 36/185*   (2006.01)
*A61K 36/06*   (2006.01)

(52) U.S. Cl.
CPC .............. *A61K 36/48* (2013.01); *A61K 36/06* (2013.01); *A61K 2236/19* (2013.01)

(58) Field of Classification Search
CPC .................... A61K 2300/00; A61K 36/06
USPC ................................. 424/757, 725
See application file for complete search history.

(56) References Cited

U.S. PATENT DOCUMENTS

| | | | |
|---|---|---|---|
| 6,372,790 | B1 | 4/2002 | Bonhomme et al. |
| 6,458,850 | B1 | 10/2002 | Sikorski et al. |
| 6,458,851 | B1 | 10/2002 | Keller et al. |
| 6,462,091 | B1 | 10/2002 | Keller et al. |
| 6,489,366 | B1 | 12/2002 | Sikorski et al. |
| 6,562,860 | B1 | 5/2003 | Keller et al. |
| 6,569,905 | B1 | 5/2003 | Sikorski et al. |
| 6,638,969 | B1 | 10/2003 | Keller et al. |
| 2003/0109558 | A1 | 6/2003 | Sikorski et al. |
| 2003/0125316 | A1 | 7/2003 | Keller et al. |
| 2003/0161910 | A1 | 8/2003 | Aoki et al. |
| 2003/0166712 | A1 | 9/2003 | Keller et al. |
| 2003/0166720 | A1 | 9/2003 | Sikorski et al. |
| 2003/0203892 | A1 | 10/2003 | Keller et al. |
| 2004/0028644 | A1 | 2/2004 | Sikorski et al. |
| 2004/0029845 | A1 | 2/2004 | Keller et al. |
| 2004/0048846 | A1 | 3/2004 | Keller et al. |
| 2004/0058908 | A1 | 3/2004 | Keller et al. |
| 2005/0241025 | A1* | 10/2005 | Takahashi et al. ........... 800/312 |
| 2007/0203246 | A1 | 8/2007 | Keller et al. |
| 2009/0029409 | A1 | 1/2009 | Soga et al. |
| 2009/0209588 | A1 | 8/2009 | Havranek et al. |
| 2011/0259743 | A1 | 10/2011 | Soga et al. |

FOREIGN PATENT DOCUMENTS

| | | |
|---|---|---|
| JO | 2007-119429 A | 5/2007 |
| JP | 59-75978 A | 4/1984 |
| JP | 05-176711 A | 7/1993 |
| JP | 06-133717 A | 5/1994 |
| JP | 2001-354558 A | 12/2001 |
| JP | 2002-502869 A | 1/2002 |
| JP | 2002-080362 A | 3/2002 |
| JP | 2002-533410 A | 10/2002 |
| JP | 2003-034636 A | 2/2003 |
| JP | 2003-277284 A | 10/2003 |
| JP | 2005-137226 A | 6/2005 |
| JP | 02005341874 A * | 12/2005 |
| JP | 2006280339 A * | 10/2006 |
| JP | 2007-192746 A | 8/2007 |
| JP | 2007-536343 A | 12/2007 |
| JP | 2008-231055 A | 10/2008 |
| JP | 2009-235068 | 10/2009 |
| JP | 2009-242382 | 10/2009 |
| JP | 2012-171923 A | 9/2012 |
| JP | 2012-171924 A | 9/2012 |
| JP | 2013-159579 A | 8/2013 |
| WO | WO 00/38724 A1 | 7/2000 |
| WO | WO 01/93696 A1 | 12/2001 |

OTHER PUBLICATIONS

International Search Report (ISR) for PCT/JP2012/054028; I.A. fd Feb. 21, 2012, mailed Mar. 19, 2012 from the Japanese Patent Office, Tokyo, Japan.
International Preliminary Report on Patentability (IPRP), Chapter I of the Patent Cooperation Treaty, including the Written Opinion for PCT/JP2012/054028; I.A. fd Feb. 21, 2012, issued Aug. 27, 2013, by the International Bureau of WIPO, Geneva, Switzerland.
Aoyama, T, "PPAR and disease," Cell (Tokyo) 31(6):218-219 (1999), Tokyo, Japan.
Kubota, N et al., "PPAR and diabetes," Cell (Tokyo) 31(6):220-224 (1999), Tokyo, Japan.
Aoyama, T, "PPAR and disorder of lipid metabolism (obesity, hyperlipidemia, fatty liver)," Cell (Tokyo) 31(6):225-228 (1999), Tokyo, Japan.
Fugii, H, "Inflammation control by PPAR," Cell (Tokyo) 31(6):218-219 (1999), Tokyo, Japan.
Schoonjan, K et al., "Role of the peroxisome proliferator-activated receptor (PPAR) in mediating the effects of fibrates and fatty acids on gene expression," J. Lipid Res., May 1996; 37: 907-925, Lipid Research, Inc., Memphis, TN.

(Continued)

*Primary Examiner* — Chris R Tate
*Assistant Examiner* — Randall Winston
(74) *Attorney, Agent, or Firm* — Sterne, Kessler, Goldstein & Fox P.L.L.C.

(57) ABSTRACT

Use of an organic solvent extract of a tempeh-fungus-fermented soybean product for the production of a PPARα and/or PPARδ activator. A method for activating PPARα and/or PPARδ, the method comprising administering an organic solvent extract of a tempeh-fungus-fermented soybean product to a subject, or feeding the organic solvent extract to the subject.

4 Claims, 3 Drawing Sheets

(56) References Cited

OTHER PUBLICATIONS

Guardiola-Diaz, HM et al, "Rat Peroxisome Proliferator-activated Receptors and Brown Adipose Tissue Function during Cold Acclimatization," J. Biol. Chem., Aug. 1999; 274: 23368-23377, Am Soc Biochem Molec Biol, Bethesda, MD.

Pineda Torra, I et al., "Peroxisome proliferator-activated receptor alpha in metabolic disease, inflammation, atherosclerosis and aging," Curr Opin Lipidol, Apr. 1999; 10(2): 151-159, Lippincott Williams & Wilkins, London, England.

Liang, F et al., "Peroxisome Proliferator Activated Receptor (PPAR)α Agonists Inhibit Hypertrophy of Neonatal Rat Cardiac Myocytes," Endocrinology, Sep. 2003; 144: 4187-4194, Endocrine Society, Chevy Chase, MD.

Yue, T-L et al., "Activation of Peroxisome Proliferator—Activated Receptor-α Protects the Heart From Ischemia/Reperfusion Injury," Circulation, Nov. 2003; 108: 2393-2399, Am Heart Assoc, Dallas, TX.

Wang, YX et al., "Peroxisome-proliferator-activated receptor δ activates fat metabolism to prevent obesity," Cell, Apr. 2003; 113(2): 159-170, Cell Press, Cambridge. MA.

Oliver, Jr., WR et al., "A selective perosisome proliferator-activated receptor δ agonist promotes reverse cholesterol transport," Proc Natl Acad Sci (USA), Apr. 2001; 98: 5306-5311, National Academy of Sciences, Washington, DC.

Tanaka, T et al., "Activation of perosisome proliferator-activated receptor δ induces fatty acid β-oxidation in skeletal muscle and attenuates metabolic syndrome," Proc Natl Acad Sci (USA), Dec. 2003; 100: 15924-15929, National Academy of Sciences, Washington, DC.

Wang, YX et al, "Regulation of muscle fiber type and running endurance by PPARδ," PLoS Biol, Oct. 2004; 2(10): E294, 1532-1539, Public Libary of Science, San Francisco, CA.

Lee, C-H et al., "PPARδ regulates glucose metabolism and insulin sensitivity," Proc Natl Acad Sci (USA), Feb. 2666; 103: 3444-3449, National Academy of Sciences, Washington, DC.

Fukui, Y et al., "A new thiazolidinedione, NC-2100, which is a weak PPAR-γ activator, exhibits potent antidiabetic effects and induces uncoupling protein 1 in white adipose tissue of KKAy obese mice," Diabetes, May 2000; 49: 759-767, Am Diabetes Assoc, Alexandria, VA.

Bhathena, SJ et al., "Beneficial role of dietary phytoestrogens in obesity and diabetes," Am J Clin Nur, Dec. 2002; 76: 1191-1201, Am Soc of Clinical Nutrition, Behtesda, MD.

Watanabe, N et al., "Effect of dietary fermented soybean on physical endurance in mice," Soy Protein Research, Japan, 2010: 13:154-158, Fuji Foundation for Protein Research, Japan.

Lan, Fei et al., "The Composition Changes in the Fermentation Process of Tempe and Its Functionality," Bulletin of Science and Technology, Jan. 31, 2009; 25(1):61-65 and 82, Zhejiang Science and Technology Assoc, China.

Xu, De-ping et al., "Machanism [sic] of Activity Enchencement [sic] of Tempe Isoflavone," Journal of Food Science and Biotechnology, May 31, 2005; 24(3):8-11, Jiangnan University, China.

Chang, C-T et al., "Effect of fermentation time on the antioxidant activities of tempeh prepared from fermented soybean using *Rhizopus oligosporus*," International Journal of Food Science & Technology, Apr. 2009, 44:799-806, Blackwell Scientific Publications, Oxford, UK.

Hirano, K et al., "Microbial metabolite such as the yeast and the physiological function," Fragrance J, 1992, (consecutive number of vol. 132), vol. 20(3):18-21, Fureguransujanaru Co. Inc., Japan.

Hoppe, MB et al., "Structure of an antioxidant from fermented soybeans (tempeh)," J Am Oil Chem Soc, 1997, 74(4):477-479, American Oil Chemists Society, Champaign, IL.

Yu, B et al., "Scavenging and anti-fatigue activity of fermented defatted soybean peptides," Eur Food Res Technol, Jan. 2008, 226:415-421, Springer, Berlin, Germany.

\* cited by examiner

SEQUENCE LISTING

```
<160> NUMBER OF SEQ ID NOS: 3

<210> SEQ ID NO 1
<211> LENGTH: 1404
<212> TYPE: DNA
<213> ORGANISM: Homo sapiens
<220> FEATURE:
<223> OTHER INFORMATION: PPAR-alpha

<400> SEQUENCE: 1
atggtggaca cggaaagccc actctgcccc ctctcccac tcgaggccgg cgatctagag      60
agcccgttat ctgaagagtt cctgcaagaa atgggaaaca tccaagagat ttcgcaatcc    120
atcggcgagg atagttctgg aagctttggc tttacggaat accagtattt aggaagctgt    180
cctggctcag atggctcggt catcacggac acgctttcac cagcttcgag cccctcctcg    240
gtgacttatc ctgtggtccc cggcagcgtg gacgagtctc ccagtggagc attgaacatc    300
gaatgtagaa tctgcgggga caaggcctca ggctatcatt acggagtcca cgcgtgtgaa    360
ggctgcaagg gcttctttcg gcgaacgatt cgactcaagc tggtgtatga caagtgcgac    420
cgcagctgca agatccagaa aaagaacaga aacaaatgcc agtattgtcg atttcacaag    480
tgcctttctg tcgggatgtc acacaacgcg attcgttttg gacgaatgcc aagatctgag    540
aaagcaaaac tgaaagcaga aattcttacc tgtgaacatg acatagaaga ttctgaaact    600
gcagatctca aatctctggc caagagaatc tacgaggcct acttgaagaa cttcaacatg    660
aacaaggtca agcccgggt catcctctca ggaaaggcca gtaacaatcc accttttgtc    720
atacatgata tggagacact gtgtatggct gagaagacgc tggtggccaa gctggtggcc    780
aatggcatcc agaacaagga ggcggaggtc cgcatctttc actgctgcca gtgcacgtca    840
gtggagaccg tcacggagct cacggaattc gccaaggcca tcccaggctt cgcaaacttg    900
gacctgaacg atcaagtgac attgctaaaa tacggagttt atgaggccat attcgccatg    960
ctgtcttctg tgatgaacaa agacgggatg ctggtagcgt atggaaatgg gtttataact   1020
cgtgaattcc taaaaagcct aaggaaaccg ttctgtgata tcatggaacc caagtttgat   1080
tttgccatga gttcaatgc actggaactg gatgacagtg atatctccct ttttgtggct   1140
gctatcattt gctgtggaga tcgtcctggc cttctaaacg taggacacat tgaaaaaatg   1200
caggagggta ttgtacatgt gctcagactc cacctgcaga gcaaccaccc ggacgatatc   1260
tttctcttcc caaaacttct tcaaaaaatg gcagacctcc ggcagctggt gacggagcat   1320
```

| | |
|---|---|
| gcgcagctgg tgcagatcat caagaagacg gagtcggatg ctgcgctgca cccgctactg | 1380 |
| caggagatct acagggacat gtac | 1404 |

```
<210> SEQ ID NO 2
<211> LENGTH: 906
<212> TYPE: DNA
<213> ORGANISM: Rattus norvegicus
<220> FEATURE:
<223> OTHER INFORMATION: PPAR-delta

<400> SEQUENCE: 2
```

| | |
|---|---|
| cacaacgcta tccgctttgg acggatgccg gaggccgaga agaggaagct ggtggcgggg | 60 |
| ctgactgcca gcgaggggtg ccagcacaac ccccagctgg ccgacctgaa ggccttctct | 120 |
| aagcacatct acaacgccta cctgaaaaac ttcaacatga ccaaaaagaa ggcccggagc | 180 |
| atcctcaccg gcaagtccag ccacaacgca cctttgtca tccacgacat cgagacactg | 240 |
| tggcaggcag agaagggcct ggtgtggaaa cagctggtga acgggctgcc gccctacaac | 300 |
| gagatcagtg tgcacgtgtt ctaccgctgc cagtccacca cagtggagac agtccgagag | 360 |
| ctcaccgagt tcgccaagaa catccccaac ttcagcagcc tcttcctcaa tgaccaggtg | 420 |
| accctcctca gtatggcgt gcacgaggcc atctttgcca tgctggcctc catcgtcaac | 480 |
| aaagacgggc tgctggtggc aacggcagt ggcttcgtca cccacgagtt cttgcgaagt | 540 |
| ctccgcaagc ccttcagtga catcattgag cccaagttcg agtttgctgt caagttcaat | 600 |
| gcgctggagc tcgatgacag tgacctggcg ctcttcatcg cggccatcat tctgtgtgga | 660 |
| gaccggccag gctcatgaa tgtgccccag gtagaagcca tccaggacac cattctgcgg | 720 |
| gctctagaat tccatctgca ggtcaaccac cctgacagcc agtacctctt ccccaagctg | 780 |
| ctgcagaaga tggcagacct gcggcagctg gtcactgagc atgcccagat gatgcagtgg | 840 |
| ctaaagaaga cggagagtga gaccttgctg cacccctgc tccaggaaat ctacaaggac | 900 |
| atgtac | 906 |

```
<210> SEQ ID NO 3
<211> LENGTH: 904
<212> TYPE: DNA
<213> ORGANISM: Homo sapiens
<220> FEATURE:
<223> OTHER INFORMATION: PPAR-gamma

<400> SEQUENCE: 3
```

| | |
|---|---|
| tcataatgcc atcaggtttg gcgatgcc acaggccgag aaggagaagc tgttggcgga | 60 |
| gatctccagt gatatcgacc agctgaatcc agagtccgct gacctccggg ccctggcaaa | 120 |
| acatttgtat gactcataca taaagtcctt cccgctgacc aaagcaaagg cgagggcgat | 180 |
| cttgacagga aagacaacag acaaatcacc attcgttatc tatgacatga attccttaat | 240 |
| gatgggagaa gataaaatca agttcaaaca catcacccc ctgcaggagc agagcaaaga | 300 |
| ggtggccatc cgcatctttc agggctgcca gtttcgctcc gtggaggctg tgcaggagat | 360 |
| cacagagtat gccaaaagca ttcctggttt tgtaaatctt gacttgaacg accaagtaac | 420 |
| tctcctcaaa tatggagtcc acgagatcat ttacacaatg ctggcctcct tgatgaataa | 480 |
| agatgggtt ctcatatccg agggccaagg cttcatgaca agggagtttc taaagagcct | 540 |
| gcgaaagcct ttggtgact ttatggagcc aagtttgag tttgctgtga agttcaatgc | 600 |
| actggaatta gatgacagcg acttggcaat atttattgct gtcattattc tcagtggaga | 660 |
| ccgcccaggt ttgctgaatg tgaagcccat tgaagacatt caagacaacc tgctacaagc | 720 |

```
cctggagctc cagctgaagc tgaaccaccc tgagtcctca cagctgtttg ccaagctgct      780
ccagaaaatg acagacctca gacagattgt cacggaacac gtgcagctac tgcaggtgat      840
caagaagacg gagacagaca tgagtcttca cccgctcctg caggagatct acaaggactt      900
gtac                                                                   904
```

PPAR ACTIVATOR

FIELD OF THE INVENTION

The present invention relates to a peroxisome proliferator activated receptor (hereinafter may be referred to as "PPAR") activator which is effective for activation of fatty acid metabolism, promotion of body fat burning, prevention and/or amelioration of obesity, suppression of fatty liver, prevention and/or amelioration of insulin resistance increase, suppression of an increase in blood glucose level, prevention and/or amelioration of arteriosclerosis, and improvement of physical endurance.

BACKGROUND OF THE INVENTION

By means of ligand-specific nuclear receptors, low-molecular-weight lipid-soluble ligands (e.g., steroid, thyroid hormone, and retinoid) are responsible for regulation of various physiological functions, including ontogenetic morphogenesis, cell proliferation and differentiation, and maintenance of biological homeostasis. In 1990, PPAR, which is a type of nuclear receptor, was identified as a protein which mediates the effect of increasing peroxisome, which is an intracellular organelle responsible for lipolysis. The protein PPARα (peroxisome proliferator activated receptor α) refers to a protein which is activated by a peroxisome proliferator. After identification of PPARα, PPARδ and PPARγ were identified as isoform genes having a structure similar to that of PPARα. Thus, PPAR is known to have three subtypes.

Each PPAR subtype is activated in a ligand-dependent manner, and controls expression of a gene having in a promoter region thereof a PPAR responsive element (PPRE) by forming a heterodimer with RXR (retinoid X receptor) whose ligand is 9-cis-retinoic acid (Non-Patent Documents 1 and 2).

For example, as has been reported, a reporter assay employing the PPRE of ACO (acyl-CoA oxidase), which is known as a key enzyme for fatty acid β-oxidation, has shown that linoleic acid, which is known as a PPAR ligand, enhances ACO transcriptional activity by the mediation of PPARα, PPARδ, or PPARγ (Non-Patent Document 3).

As described hereinbelow, in recent years, PPAR has been elucidated to be involved in many physiological and pathological phenomena.

Specifically, the function of PPARα is considered to be widely involved in biological energy metabolism or homeostasis, such as synthesis, transportation, or secretion of fatty acids, or ATP production in a fat-consuming organ. Particularly, it has been elucidated that expression of the gene of a β-oxidation-related enzyme important for fatty acid metabolism (e.g., ACO, HMG-CoA synthase, acyl-CoA synthase, medium chain acyl-CoA dehydrogenase, fatty acid binding protein, or lipoprotein lipase) is strongly dependent on activation of PPARα. PPARα is highly expressed in the liver, heart, kidney, etc., and a PPARα activator is widely recognized as being effective for activation of lipid metabolism in such an organ.

Activation of fatty acid metabolism in association with activation of PPARα is thought to lead to decomposition of liver fat, amelioration of fatty liver, promotion of decomposition or burning of body fat (e.g., visceral fat or subcutaneous fat), and suppression of obesity. A fibrate drug, which is known as a PPARα activator, has been shown to exhibit the effect of promoting fatty acid burning and the effect of increasing HDL cholesterol level, and has recently been elucidated to exhibit, for example, the effect of increasing expression of an adiponectin receptor. Thus, a fibrate drug has been widely used as a therapeutic drug for hyperglycemia with non-insulin-dependent diabetes, dyslipidemia, hyperglycemia, atherosclerosis, etc. (Non-Patent Document 4 and Patent Documents 1 and 2). Meanwhile, PPARα activators have been reported to be effective for cardiac hypertrophy and ischemic heat disease (Non-Patent Documents 5 and 6).

Therefore, PPARα activators are considered to be widely effective for activation of fatty acid metabolism, promotion of body fat burning, prevention and/or amelioration of obesity, prevention and/or amelioration of dyslipidemia, prevention and/or amelioration of fatty liver, prevention and/or amelioration of insulin resistance increase or diabetes, prevention and/or amelioration of arteriosclerosis, prevention and/or amelioration of cardiac hypertrophy or ischemic heat disease, etc. Also, in recent years, search and development have been actively performed on PPARα activators (Patent Documents 3 to 5).

PPARδ (also called PPARβ, NUC1, or FAAR) was cloned in 1992, and, since then, the function thereof has been unknown for a long period of time. However, in recent years, PPARδ has been elucidated to have various physiological functions through, for example, studies employing genetically modified animals and development of PPARδ-selective agonists. Studies employing mice in which PPARδ is overexpressed have shown that PPARδ suppresses an increase in body weight caused by high-fat diet load, reduces fat weight, reduces blood triglyceride level, or suppresses fatty liver (Non-Patent Document 7). In an experiment in which GW501516 (i.e., a PPARδ-selective agonist) was administered to obese rhesus monkeys, HDL cholesterol level was increased, and triglyceride level and LDL cholesterol level were reduced (Non-Patent Document 8).

Studies on the effect of GW501516-acted skeletal-muscle-derived cells on gene expression have shown that GW501516 induces fatty acid uptake or transportation, or expression of fatty acid metabolism-related genes of mitochondrial β-oxidation enzymes, uncoupling proteins, etc. Also, studies have shown that, in GW501516-administered mice, an increase in body weight caused by high-fat diet load is suppressed, fat weight is reduced, and insulin resistance is ameliorated, as in the case of mice in which adipose tissue-specific PPARδ is overexpressed. In the skeletal muscle of the GW501516-administered mice, induction of fatty acid metabolism-related genes and fatty acid β-oxidation was determined. Therefore, conceivably, activation of PPARδ increases energy consumption in skeletal muscle, which results in suppression of fat accumulation in peripheral tissues, whereby insulin resistance is ameliorated (Non-Patent Document 9). Also, since administration of GW501516 to genetically obese mice suppresses pancreatic islet hypertrophy, GW501516 is considered to have a pancreatic islet protection effect (Non-Patent Document 9).

As has been reported, overexpression of PPARδ in mice in a skeletal muscle-specific manner suppresses obesity or insulin resistance increase. As has also been shown, surprisingly, the amount of so-called "slow-twitch muscle" (or "red muscle") (i.e., high-endurance muscle fiber containing much mitochondria) is considerably increased in the skeletal muscle of the mice, and thus the mice have excellent physical endurance; i.e., the mice can run for a distance about twice that in the case of control mice (Non-Patent Document 10). Therefore, conceivably, activation of PPARδ is effective for improvement of exercise endurance.

According to a recent report, PPARδ controls insulin sensitivity in the liver. In a suggested mechanism for this control, activation of PPARδ reduces supply of glucose from the liver via activation of a hepatic glycolytic pathway and a pentose phosphate cycle, thereby enhancing insulin sensitivity (Non-Patent Document 11).

As described above, activation of PPARδ leads to an increase in HDL cholesterol level, a reduction in LDL cholesterol level, suppression of obesity, amelioration of insulin resistance/enhancement of insulin sensitivity, activation of fatty acid metabolism, promotion of body fat burning, a reduction in blood triglyceride level, suppression of fatty liver, improvement of physical endurance, etc. Therefore, a PPARδ activator is considered to be effective as a preventive and/or ameliorating agent for arteriosclerosis, a preventive and/or ameliorating agent for obesity, an agent for prevention and/or amelioration of insulin resistance increase, an agent for activation of fatty acid oxidation, an agent for promotion of body fat burning, a preventive and/or ameliorating agent for dyslipidemia, a preventive and/or ameliorating agent for fatty liver, or a physical-endurance-improving agent.

In view of the foregoing, search and development, have been actively performed on PPARδ activators, and flavone compounds, phenoxyacetic acid derivatives, etc have been reported so far (Patent Documents 6 and 7).

PPARγ is a molecule which acts on energy storage in a nutrient-rich state, and serves as a so-called thrifty gene. Particularly, PPARγ2 is expressed with relatively high specificity to adipocytes, and PPARγ2 has been elucidated to play a central role in adipocyte differentiation. As has been shown, a thiazolidine derivative, which is known as a PPARγ ligand, strongly induces adipocyte differentiation, to thereby reduce adipocyte size and to enhance insulin sensitivity. Therefore, a thiazolidine derivative has been widely used as an ameliorating agent for insulin resistance or a therapeutic drug for diabetes. However, problems may arise in that administration of a thiazolidine derivative increases body weight or fat weight, and induces obesity (Non-Patent Document 12).

Thus, conceivably, PPAR activators are widely effective for activation of fatty acid metabolism, promotion of body fat burning, prevention and/or amelioration of obesity, prevention and/or amelioration of dyslipidemia, prevention and/or amelioration of fatty liver, improvement of physical endurance, prevention and/or amelioration of insulin resistance increase or diabetes, prevention and/or amelioration of arteriosclerosis, prevention and/or amelioration of cardiac hypertrophy or ischemic heat disease, etc., and are also effective for prevention and/or amelioration of so-called lifestyle-related diseases or metabolic syndrome.

Tempeh is an Indonesian, traditional, fermented soybean food, and this nutrient-rich food contains proteins, dietary fiber, amino acids, vitamins (vitamin E and vitamin B complex), minerals (e.g., iron), isoflavones, etc. (Patent Document 8). The fermented food tempeh is produced by fermenting soybeans with the tempeh fungus. In view of the efficacy of the components contained in tempeh, tempeh has been suggested to exhibit the effect of suppressing an, increase in cholesterol level, the effect of preventing liver fat accumulation, anti-obesity effect, hemolysis preventing effect, and intestinal regulation effect (Patent Document 8). As has been reported, tempeh contains, at a high concentration, γ-aminobutyric acid, which is known to have the effect of suppressing an increase in blood pressure, the effect of reducing neutral lipid, anti-obesity effect, tranquilizing effect, the effect of ameliorating menopausal symptoms, sleep-promoting effect, alcohol/aldehyde-metabolizing effect, and deodorizing effect (Patent Document 9).

However, it has not been known that an organic solvent extract of a soybean product fermented with the tempeh fungus (hereinafter may be referred to as a "tempeh-fungus-fermented soybean product") is responsible for PRAR activation, and is effective for, for example, activation of fatty acid metabolism or promotion of body fat burning.

CITATION LIST

Patent Document

Patent Document 1: Japanese Kohyo Patent Publication No. 2002-502869
Patent Document 2: Japanese Kohyo Patent Publication No. 2002-533410
Patent Document 3: JP-A-2001-354558
Patent Document 4: JP-A-2002-80362
Patent Document 5: JP-A-2003-34636
Patent Document 6: JP-A-2007-119429
Patent Document 7: Japanese Kohyo Patent Publication No. 2007-536343
Patent Document 8: JP-A-1994-133717.
Patent Document 9: WO2001/093696

Non-Patent Document

Non-Patent Document 1: Saibo: 31 (6), 218-234, 1999
Non-Patent Document 2: J. Lipid Res. 37, 907-925, 1996
Non-Patent Document 3: J. Biol. Chem. 274, 23368-23377, 1999
Non-Patent Document 4: Curr. Opin. Lipidol. 10, 151-159, 1999
Non-Patent Document 5: Endcrinology 144, 4187-4194, 2003
Non-Patent Document 6: Circulation 108, 2393-2399, 2003
Non-Patent Document 7: Cell. 113, 159-170, 2003
Non-Patent Document 8: Proc. Natl. Acad. Sci. USA. 98, 530.6-5311, 2001
Non-Patent Document 9: Proc. Natl. Acad. Sci. USA, 100, 15924-15929, 2003
Non-Patent Document 10: PloS Biol. 2, e294, 2004
Non-Patent Document 11: Proc. Natl. Acad. Sci. USA. 103, 3444-3449, 2006
Non-Patent Document 12: Diabetes. 49, 759-767, 2000

SUMMARY OF THE INVENTION

In one aspect, the present invention provides use of an organic solvent extract of a tempeh-fungus-fermented soybean product for the production of a PPARα and/or PPARδ activator.

In another aspect, the present invention provides use of an organic solvent extract of a tempeh-fungus-fermented soybean product for the production of a physical-endurance-improving agent.

In yet another aspect, the present invention provides use of an organic solvent extract of a tempeh-fungus-fermented soybean product for the production of an agent for prevention and/or amelioration of insulin resistance increase.

In yet another aspect, the present invention provides use of an organic solvent extract of a tempeh-fungus-fermented soybean product for the production of an agent for PPARα and/or PPARδ-activation-derived prevention and/or amelioration of obesity.

In yet another aspect, the present invention provides use of an organic solvent extract of a tempeh-fungus-fermented soybean product for the production of an agent for PPARα and/or PPARδ-activation-derived prevention and/or amelioration of arteriosclerosis.

In yet another aspect, the present invention provides a method for activating PPARα and/or PPARδ, the method comprising administering an organic solvent extract of a tempeh-fungus-fermented soybean product to a subject in need of improvement of physical endurance, or feeding the organic solvent extract to the subject.

In yet another aspect, the present invention provides a method for improving physical endurance, the method comprising administering an organic solvent extract of a tempeh-fungus-fermented soybean product to a subject in need of improvement of physical endurance, or feeding the organic solvent extract to the subject.

DETAILED DESCRIPTION OF THE INVENTION

Figure 1:
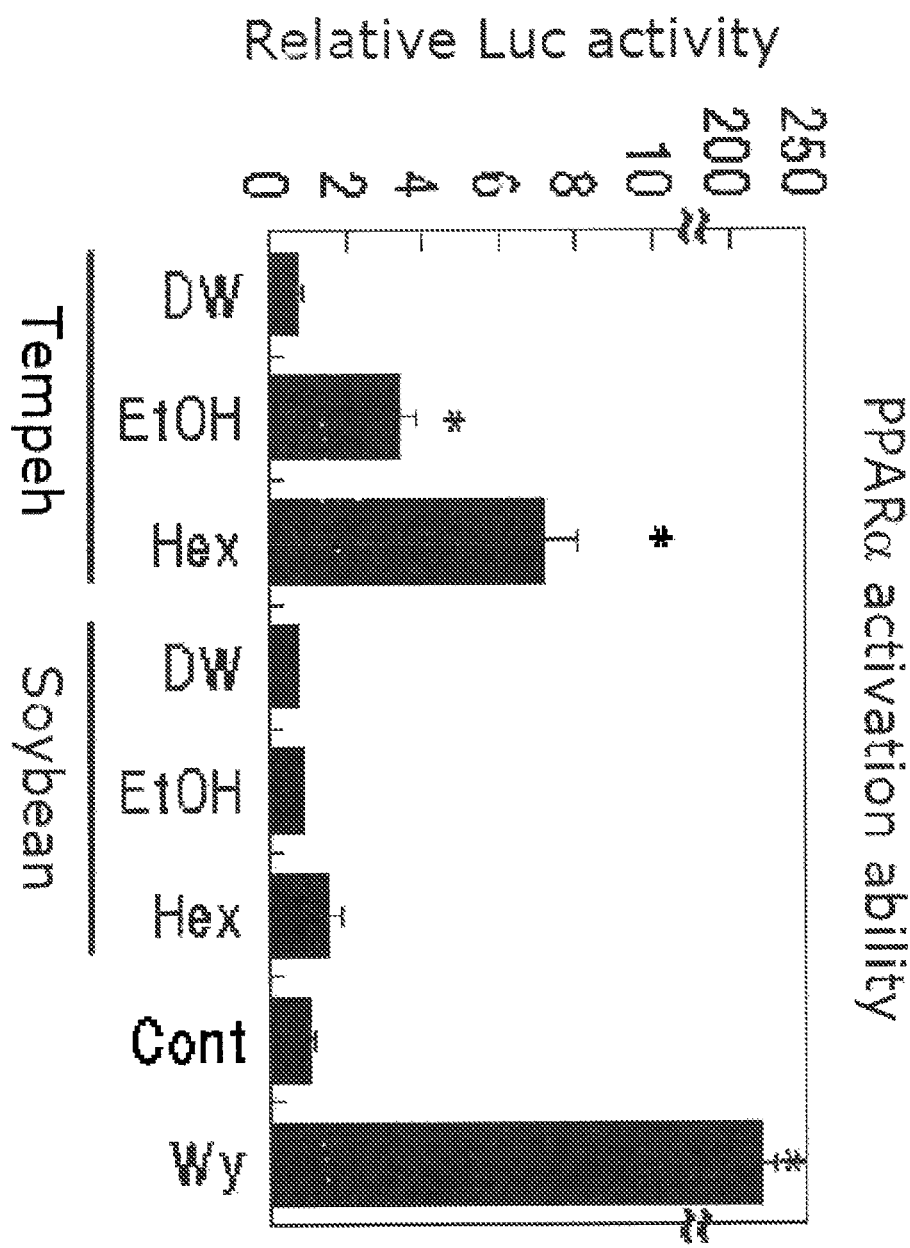
FIG. 1 is a graph showing PPARα activation ability (wherein DW represents a water extract; EtOH represents a 50% ethanol extract; Hex represents a hexane extract; Cont represents a solvent control; Wy represents Wy14543; and * represents a significant difference (P<0.05) with respect to the solvent control).

The present invention relates to provision of a food, drug, or quasi drug which exhibits an excellent PPAR-activating effect and high safety.

The present inventors found that, among widely eaten natural food materials, an organic solvent extract of a tempeh-fungus-fermented soybean product exhibits a PPARα-activating effect and a PPARδ-activating effect, and is useful as an active ingredient incorporated into a food, drug, or quasi drug which exhibits the effect of activating fatty acid metabolism, promoting body fat burning, preventing and/or ameliorating insulin resistance increase, improving physical endurance, suppressing obesity, suppressing fatty liver, preventing and/or ameliorating arteriosclerosis, or preventing and/or ameliorating cardiac hypertrophy or ischemic heat disease.

The PPAR activator of the present invention exhibits an excellent PPAR-activating effect, and also exhibits high safety even when taken for a long period of time. Therefore, the PPAR activator is useful as an active ingredient incorporated into a food or beverage, drug, or quasi drug which exhibits the effect of activating fatty acid metabolism, promoting body fat burning, preventing and/or ameliorating insulin resistance increase, improving physical endurance, preventing and/or ameliorating obesity, suppressing fatty liver, preventing and/or ameliorating arteriosclerosis, or preventing and/or ameliorating cardiac hypertrophy or ischemic heat disease.

As used herein, the term "tempeh-fungus-fermented soybean product" collectively refers to tempeh (i.e., Indonesian traditional, fermented soybean food) and products produced by fermenting soybeans with the tempeh fungus. The tempeh-fungus-fermented soybean product employed in the present invention may be produced through, for example, the below-described procedure (i.e., fermentation of soybeans with the tempeh fungus). Alternatively, any commercially available tempeh-fungus-fermented soybean product (e.g., tempeh or okara tempeh) may be purchased and employed.

No particular limitation is imposed on the tempeh fungus employed in the present invention, so long as it is generally used for production of tempeh. For example, the tempeh fungus employed may be a fungus belonging to the genus *Rhizopus* (i.e., filamentous fungus), and is preferably *Rhizopus oligosporus, Rhizopus oryza*, etc.

As used herein, the term "soybean" refers to a seed of soybean, which is an annual herb of the genus *Glycine* belonging to the family Fabaceae. No particular limitation is imposed on the variety and production area of the soybean employed as a raw material in the present invention, so long as it is employed as the raw material of an edible product or a processed food. As in the case of a general method for the production of tempeh, preferably, soybeans are immersed in an acidic solution, and thermally treated together with water or steam before fermentation. Preferably, soybeans are subjected to peeling treatment so that soybean hulls do not remain in a raw material employed. Peeled, soybeans may be employed as a raw material, or the peeling treatment may be carried out after immersion of soybeans in an acidic solution or after thermal treatment of the soybeans.

The acidic solution employed may be, for example, an aqueous solution containing an edible organic acid (e.g., acetic acid, lactic acid, citric acid, or tartaric acid), or an aqueous solution containing a food containing such an acid (e.g., vinegar). Preferably, the amount of an acid or acid-containing food employed is adjusted to fall within such a range that growth of saprophytes on soybeans can be suppressed, and growth of the tempeh fungus is not inhibited. When, for example, acetic acid is employed, the amount thereof is preferably adjusted to 0.2 to 0.5% by weight. No particular limitation is imposed on the time for thermal treatment of soybeans. When soybeans are subjected to boiling treatment, the treatment time is generally 30 to 90 minutes, preferably 30 to 60 minutes.

Subsequently, the tempeh fungus is inoculated onto the above treated soybeans for fermentation. No particular limitation is imposed on the amount of the tempeh fungus inoculated. The amount of the tempeh fungus inoculated onto the thermally treated and cooled soybeans is generally 0.1 to 3.0% by weight, preferably 0.2 to 0.5% by weight, with respect to that of the soybeans.

No particular limitation is imposed on the temperature during fermentation, but the temperature is preferably 20 to 45° C. more preferably 30 to 37° C., much more preferably 31 to 32° C. The humidity during fermentation is preferably 60% to 99%, more preferably 80 to 98%.

The fermentation time, which may vary with, for example, the fermentation temperature or the amount of the tempeh fungus inoculated, is preferably 10 to 50 hours, more preferably 15 to 30 hours, much more preferably 20 to 28 hours.

The tempeh-fungus-fermented soybean product of the present invention can be produced through fermentation under the aforementioned conditions. The thus-produced tempeh-fungus-fermented soybean product may be employed as is for extraction, or may be dried before extraction.

The organic solvent employed for obtaining an extract from the tempeh-fungus-fermented soybean product may be a hydrophilic solvent or a hydrophobic solvent. Although these solvents may be employed in combination, a hydrophobic solvent is preferably employed.

Examples of the organic solvent include alcohols such as methanol, ethanol, n-propanol, isopropanol, n-butanol, and isobutanol; polyhydric alcohols such as ethylene glycol, propylene glycol, and butylene glycol; hydrocarbons such as hexane, cyclohexane, and petroleum ether; nitriles such as acetonitrile, propionitrile, and benzonitrile; ketones such as acetone and methyl ketone; esters such as methyl acetate and ethyl acetate; linear-chain and cyclic ethers such as tetrahydrofuran and diethyl ether; polyethers such as polyethylene glycol; halogenated hydrocarbons such as dichloromethane, chloroform, and carbon tetrachloride; aromatic hydrocarbons such as benzene and toluene; pyridines; supercritical carbon dioxide; fat or oil; waxes; and other oils. These solvents may be employed singly or in combination of two or more species. Extraction may be repeatedly carried out by use of different solvents (e.g., an alcohol extract may be subjected to further extraction with another organic solvent).

Of these solvents, an alcohol, hexane, and a solvent mixture of water and a lower alcohol are preferred; a solvent mixture of water and ethanol, ethanol, and hexane are more preferred; and hexane is much more preferred.

The alcohol employed is preferably a C1 to C5 lower alcohol, more preferably a C1 to C4 lower alcohol, much more preferably a C1 to C3 alcohol.

The ratio by volume of water to an alcohol; i.e., water/alcohol, is preferably 100/1 to 1/100, more preferably 90/1 to 1/100, much more preferably 2/1 to 1/100.

When, for example, a PPARα and/or PPARδ-activating substance is extracted from the tempeh-fungus-fermented soybean product with a solvent mixture of water and ethanol, a 0.01 to 100% by volume aqueous ethanol solution is preferably employed, a 10 to 100% by volume aqueous ethanol solution is more preferably employed, a 30 to 100% by volume aqueous ethanol solution is much more preferably employed, a 50 to 100% by volume aqueous ethanol solution is much more preferably employed.

The organic solvent extract of the tempeh-fungus-fermented soybean product employed in the present invention is produced by subjecting the tempeh-fungus-fermented soybean product to extraction with an organic solvent at ambient temperature (0 to 30° C.) or under heating conditions.

Preferably, the organic solvent is employed in an amount of ½ to 10 parts by mass on the basis of 1 part by mass of the tempeh-fungus-fermented soybean product. The extraction temperature is preferably 0 to 40° C., more preferably 10 to 30° C. The extraction time is preferably 1/10 to 12 hours, more preferably ½ to 5 hours.

The extraction technique employed may be, for example, solid-liquid extraction, immersion, decoction, percolation, reflux extraction, ultrasonic extraction, microwave extraction, or stirring. Preferably, solid-liquid extraction is carried out under stirring.

The thus-produced extract may be employed as is after removal of the solvent. However, the extract may be subjected to any known separation/purification technique, such as treatment with activated carbon, liquid-liquid, partition, column chromatography, liquid chromatography, gel filtration, or precise distillation, and then diluted with an appropriate solvent; i.e., the extract may be employed as diluted solution. Alternatively, the extract may be prepared as concentrated extract, dry powder, or paste.

As described in the Examples hereinbelow, the organic solvent extract of the tempeh-fungus-fermented soybean product—which is prepared through extraction, with an organic solvent, of a fermented product produced by fermenting soybeans with the tempeh fungus—exhibits the effect of enhancing the transcriptional activity of a gene dependent on PPARα and/or PPARδ. As described above, PPARα and/or PPARδ is widely involved in biological energy metabolism or homeostasis. Particularly, expression of the gene of a β-oxidation-related enzyme important for lipid metabolism (e.g., ACO, HMG-CoA synthase, acyl-CoA synthase, medium chain acyl-CoA dehydrogenase, fatty acid binding protein, or lipoprotein lipase) is strongly dependent on activation of PPARα and/or PPARδ (Non-Patent Documents 1 to 10 and Patent Documents 1 to 7). Therefore, the tempeh-fungus-fermented soybean product or an extract thereof is widely effective for activation of fatty acid metabolism, promotion of body fat burning, prevention and/or amelioration of obesity, prevention and/or amelioration of dyslipidemia, prevention and/or amelioration of fatty liver, improvement of physical endurance, prevention and/or amelioration of insulin resistance increase or diabetes, prevention and/or amelioration of arteriosclerosis, prevention and/or amelioration of cardiac hypertrophy or ischemic heat disease, etc.

Thus, since the organic solvent extract of the tempeh-fungus-fermented soybean product exhibits a PPARα-activating effect and/or a PPARδ-activating effect, the organic solvent extract can be employed for activation of PPARα and/or PPARδ; for improvement of physical endurance; for activation of fatty acid metabolism; for promotion of body fat burning; or for prevention and/or amelioration of diabetes, insulin resistance increase, obesity, or arteriosclerosis.

In exemplary modes, the organic solvent extract of the tempeh-fungus-fermented soybean product may be employed as a PPARα and/or PPARδ activator, a fatty acid metabolism activator, an agent for promoting body fat burning, a preventive and/or ameliorating agent for diabetes, an agent for prevention and/or amelioration of insulin resistance increase, a preventive and/or ameliorating agent for obesity, a preventive and/or ameliorating agent for arteriosclerosis, or a physical-endurance-improving agent (hereinafter these agents may be collectively referred to as "PPAR activator, etc."). Alternatively, the organic solvent extract of the tempeh-fungus-fermented soybean product may be employed for production of the PPAR activator, etc. The effects by these agents (i.e., the effect of activating fatty acid metabolism, the effect of promoting body fat burning, the effect of improving physical endurance, and the effect of preventing and/or ameliorating diabetes, insulin resistance increase, obesity, or arteriosclerosis) are provided through activation of PPARα and/or PPARδ.

The PPAR activator, etc. may be employed as an active ingredient of a human or animal food, drug, quasi drug, or cosmetic product exhibiting any of the aforementioned effects; i.e., activation of PPARα or PPARδ, activation of fatty acid metabolism, promotion of body fat burning, suppression of fatty liver, prevention and/or amelioration of diabetes, prevention and/or amelioration of insulin resistance increase, prevention and/or amelioration of obesity, prevention and/or amelioration of arteriosclerosis, improvement of physical endurance, etc. Also, the organic solvent extract of the tempeh-fungus-fermented soybean product may be applied to, for example, a food, functional food, patient's diet, food for specified health use, or pet food which has any of the following concepts and optionally displays the concept activation of PPARα or PPARδ, activation of fatty acid metabolism, promotion of body fat burning, suppression of fatty liver, prevention and/or amelioration of diabetes, prevention and/or amelioration of insulin resistance increase, prevention and/or amelioration of obesity, prevention and/or amelioration of arteriosclerosis, improvement of physical endurance, etc.

Also, the present invention provides a method for the production of a PPARα and/or PPARδ activator, the method including fermenting soybeans with the tempeh fungus, and preparing an extract from the resultant fermented product with an organic solvent. Also, the present invention provides a method for the production of, for example, a fatty acid metabolism activator, an agent for promoting body fat burning, a preventive and/or ameliorating agent for diabetes, an agent for prevention and/or amelioration of insulin resistance increase, a preventive and/or ameliorating agent for obesity, a preventive and/or ameliorating agent for arteriosclerosis, or a physical-endurance-improving agent, the method including fermenting soybeans with the tempeh fungus, and preparing an extract from the resultant fermented product with an organic solvent.

When the PPAR activator, etc. of the present invention are employed as an active ingredient of a drug or a quasi drug, the dosage form of the drug or the quasi drug may be, for example, an oral dosage form such as tablet, capsule, granule, powder, or syrup; or a parenteral dosage form such as injection, suppository, inhalant, transdermal agent, or external-use agent.

For preparation of drug products having the aforementioned various dosage forms, the organic solvent extract of the tempeh-fungus-fermented soybean product of the present invention may be employed singly, or in appropriate combination with another pharmaceutically acceptable ingredient such as an excipient, a binder, an extender, a disintegrant, a surfactant, a lubricant, a dispersant, a buffer, a preservative, a flavoring agent, a perfume, a coating agent, a carrier, or a diluent.

Among the aforementioned dosage forms, an oral dosage form is preferred. An oral liquid drug product may be produced through a customary method by mixing the organic solvent extract of the tempeh-fungus-fermented soybean product with, for example, a flavoring agent, a buffer, or a stabilizer.

When the PPAR activator, etc. of the present invention are employed as an active ingredient of a cosmetic product, the cosmetic product may be provided as, for example, a skin external-use agent, a detergent, a bath agent, or a makeup cosmetic composition. The cosmetic product, whose form may vary with the intended use thereof, may be provided in various forms, including beauty lotion, skin lotion, massaging agent, lotion, emulsion, gel, cream, ointment, powder, pack, cataplasm, granule, foundation, lipstick, shampoo, conditioner, hair tonic, tablet, capsule, and sheet-like product. For preparation of cosmetic products having the aforementioned various forms, the organic solvent extract of the tempeh-fungus-fermented soybean product of the present invention may be employed singly, or in appropriate combination with any ingredient which may be incorporated into a cosmetic composition, such as an external-use base, oil, or oily substance, a humectant, a powder, a pigment, an emulsifier, a solubilizer, a detergent, a UV absorbent, a thickener, a pharmaceutically active ingredient, a perfume, a resin, an antibacterial/antifungal agent, an alcohol, a chelate, an inorganic acid, an organic acid, a vitamin, a water-soluble polymer, or a surfactant.

When the PPAR activator, etc. of the present invention are employed as an active ingredient of a food, the food may be provided in any product form, for example, bread, cake, noodle, confectionery, jelly, frozen food, ice cream, dairy product, beverage, or soup, or may be provided in a form similar to that of the aforementioned oral drug product (e.g., tablet, capsule, or syrup).

Examples of the beverage include fruit juice beverage, carbonated beverage, tea beverage, near water beverage, sports beverage, milk beverage, alcoholic beverage, and refreshing beverage. Such a beverage may be provided as a container-filled beverage.

Examples of the edible oil include oil and fat processed products such as cooking oil, seasoning, mayonnaise, dressing, and margarine; and pasta sauces.

For preparation of food products having the aforementioned various forms, the PPAR activator, etc. of the present invention may be employed singly, or in appropriate combination with another food material, a solvent, a softener, an oil, an emulsifier, a preservative, a flavor, a stabilizer, a colorant, an antioxidant, a humectant, or a thickener. Examples of the food products include foods for activation of $PPAR\alpha$ and/or $PPAR\delta$, foods for activation of fatty acid metabolism, foods for prevention and/or amelioration of obesity, foods for suppression of fatty liver, foods for prevention and/or amelioration of diabetes, foods for prevention and/or amelioration of insulin resistance increase, foods for prevention and/or amelioration of arteriosclerosis, foods for suppression of an increase in blood glucose level, foods for improvement of physical endurance, and pet foods.

When the PPAR activator, etc. are incorporated into any of the aforementioned products, the amount of the PPAR activator, etc. may vary with the form of the product. When, for example, the PPAR activator, etc. are incorporated in a food product, the amount of the PPAR activator, etc (as reduced to dried tempeh-fungus-fermented soybean product extract) is generally 0.0001 to 10% by mass, preferably 0.001 to 5% by mass, more preferably 0.002 to 2% by mass, with respect to the entire composition of the food product.

When, for example, the PPAR activator, etc. are incorporated in a beverage product, the amount of the PPAR activator, etc. (as reduced to dried tempeh-fungus-fermented soybean product extract) is preferably 0.001 to 0.5% by mass, more preferably 0.005 to 0.25% by mass, much more preferably 0.01 to 0.1% by mass, with respect to the entire composition of the beverage product. When the PPAR activator, etc. are incorporated in an edible tablet and/or a capsule, the amount of the PPAR activator, etc. (as reduced to dried tempeh-fungus-fermented soybean product extract) is preferably 0.1 to 95% by mass, more preferably 1 to 90% by mass, much more preferably 5 to 50% by mass, with respect to the entire composition of the tablet and/or the capsule.

When the PPAR activator, etc are incorporated in a drug product other than the aforementioned ones (e.g., an oral solid drug product such as a tablet, a granule, or a capsule, or an oral liquid drug product such as a solution or a syrup), the amount of the PPAR activator, etc. as reduced to dried tempeh-fungus-fermented soybean product extract) is generally 0.01 to 95% by mass, preferably 5 to 90% by mass, more preferably 10 to 50% by mass, with respect to the entire composition of the drug product.

When the PPAR activator, etc. are incorporated in a cosmetic product, the amount of the PPAR activator, etc. (as reduced to dried tempeh-fungus-fermented soybean product extract) is generally 0.00001 to 5% by mass, preferably 0.0001 to 3% by mass, more preferably 0.001 to 1% by mass, with respect to the entire composition of the cosmetic product.

The daily dose (effective ingestion amount) of the PPAR activator, etc. (as reduced to dried tempeh-fungus-fermented soybean product extract) is preferably 1 to 5,000 mg/60 kg body weight, more preferably 5 to 3,000 mg/60 kg body weight, much more preferably 10 to 2,000 mg/60 kg body weight, much more preferably 100 to 1,000 mg/60 kg body weight.

Through administration or ingestion of the PPAR activator, etc. of the present invention, PPARα and/or PPARδ can be activated, which leads to, for example, activation of fatty acid metabolism, promotion of body fat burning, prevention and/or amelioration of obesity, prevention and/or amelioration of dyslipidemia, prevention and/or amelioration of fatty liver, improvement of physical endurance, prevention and/or amelioration of insulin resistance increase or diabetes, or prevention and/or amelioration of arteriosclerosis. Thus, a method therefor may employ the PPAR activator, etc. of the present invention. No particular limitation is imposed on the subject for administration or injection of the PPAR activator, etc., so long as the subject is a human or animal requiring the PPAR activator, etc Examples of the subject include patients with obesity, dyslipidemia, fatty liver, insulin resistance, diabetes, and arteriosclerosis; those who are likely to develop such a disease; and those with reduced physical endurance.

As used herein, the expression "subject who requires improvement of physical endurance" encompasses, for example, athletes who require higher physical endurance; those suffering from reduced physical endurance in daily life as a result of aging, disease, or disorder and those who, even young (e.g., the age of 64 or younger) or healthy, have reduced physical endurance not caused by aging, disease, or disorder, but caused by insufficient exercise in daily life for the reasons of, for example, busy schedules (e.g., job, school work, and childcare) and dislike of exercise. As used herein, the term "physical endurance" refers to physical endurance required during exercise.

As used herein, the term "athlete" refers to those who have inherent or acquired physical features required for exercise or sports (e.g., strength, agility, and physical endurance); in particular, professional sports players, or amateur players who belong to a sports club, etc. and aim at participation in, a competition, etc.

As used herein, the expression "those suffering from reduced physical endurance in daily life" refers to, for example, those who encounter difficulty in taking actions in daily life, such as climbing stairs at home or in a station, and walking to a supermarket for shopping.

As used herein, the term "exercise in daily life" refers to a physical activity incorporated into daily routine. The purpose of the exercise is to improve general health status and physical strength. The term "exercise" as used herein does not include mild activities (basic activities) in daily life, such as standing, slow walking, and lifting of lightweight objects. Those who perform only such a basic activity are regarded as not doing exercise.

As used herein, the expression "insufficient exercise in daily life" may refer to a state where the amount of exercise is less than that recommended by the American CDC (Centers for Disease Control and Prevention). For example, according to the "2008 Physical Activity Guidelines for Americans" by the American CDC, the recommended amount of exercise per week for adults (the age of 17 to 64) is any of the following (A) to (C):

(A) 2 hours and 30 minutes (150 minutes) of moderate-intensity aerobic activity (i.e., brisk walking) every week, and muscle-strengthening activities (by weight training) on two or more days a week that work all major muscle groups (legs, hips, back, abdomen, chest, shoulders, and arms); or (B) 1 hour and 15 minutes (75 minutes) of vigorous-intensity aerobic activity (i.e., jogging or running) every week, and muscle-strengthening activities (by weight training) on two or more days a week that work all major muscle groups (legs, hips, back, abdomen, chest, shoulders, and arms); or (C) an equivalent mix of moderate- and vigorous-intensity aerobic activity, and muscle-strengthening activities (by weight training) on two or more days a week that work all major muscle groups (legs, hips, back, abdomen, chest, shoulders, and arms).

EXAMPLES

Production Example 1

Preparation of Hexane Extract of Tempeh

Tempeh (Mariza, commercially available product) (50 g) was pulverized, and hexane (100 mL) was added thereto. The resultant mixture was stirred at room temperature (20° C.) for two hours, and the resultant hexane phase was separated through filtration. Thereafter, the hexane phase was concentrated by means of a rotary evaporator, to thereby produce an extract (0.42 g). Subsequently, the extract was dissolved in ethanol so as to achieve a concentration of 1% (w/v).

Production Example 2

Preparation of 50% Ethanol Extract of Tempeh

Tempeh (Mariza, commercially available product) (50 g) was pulverized, and 50% ethanol (100 mL) was added thereto. The resultant mixture was stirred at room temperature (20° C.) for two hours, followed by filtration. The resultant filtrate was concentrated by means of a rotary evaporator, to thereby produce an extract (1.70 g). Subsequently, the extract was dissolved in ethanol so as to achieve a concentration of 1% (w/v).

Comparative Production Example 1

Preparation of Water Extract of Tempeh

Tempeh (Mariza, commercially available product) (50 g) was pulverized, and water (100 mL) was added thereto. The resultant mixture was stirred at room temperature (20° C.) for two hours, followed by filtration. The resultant filtrate was concentrated through lyophilization, to thereby produce an extract (1.61 g). Subsequently, the extract was dissolved in ethanol so as to achieve a concentration of 1% (w/v).

Comparative Production Example 2

Preparation of Hexane Extract of Soybean

Hexane (50 mL) was added to steamed soybeans (20 g), and the resultant mixture was stirred at room temperature (20° C.) for two hours. The resultant hexane phase was separated through filtration, and then concentrated by means of a rotary evaporator, to thereby produce an extract (0.10 g). Subsequently, the extract was dissolved in ethanol so as to achieve a concentration of 1% (w/v).

Comparative Production Example 3

Preparation of Water Extract of Soybean

Water (50 mL) was added to steamed soybeans (20 g), and the resultant mixture was stirred at room temperature (20° C.) for two hours, followed by filtration. The resultant filtrate was concentrated through lyophilization, to thereby produce an extract (0.68 g). Subsequently, the extract was dissolved in ethanol so as to achieve a concentration of 1% (w/v).

Comparative Production Example 4

Preparation of 50% Ethanol Extract of Soybean

50% Ethanol (50 mL) was added to steamed soybeans (20 g), and the resultant mixture was stirred at room temperature (20° C.) for two hours, followed by filtration. The resultant filtrate was concentrated by means of a rotary evaporator, to thereby produce an extract (0.64 g). Subsequently, the extract was dissolved in ethanol so as to achieve a concentration of 1% (w/v).

The thus-prepared extracts were employed as test substances in the below-described Examples 1 to 3.

Example 1

PPARα Activation Test

A PPARα ligand binding site (NCBI PefSeq NM_001001929, nt183-1586, SEQ ID NO: 1) was amplified through PCR by use of Human colon total RNA (Clontech). The PCR amplified product was cloned into pCR Blunt (Invitrogen), and a DNA fragment was prepared through treatment with restriction, enzymes (MluI, KpnI; Takara). The thus-prepared DNA fragment was inserted into a multi-cloning site (MluI/KpnI) of pBIND vector (Promega), to thereby produce pBIND-PPARα LED. When this vector is incorporated into cells, a fusion protein of the PPARα ligand binding site and the GAL4 DNA binding site is expressed. The fusion protein binds to the GAL4-binding sequence through binding to the PPARα ligand, thereby activating transcription of a gene downstream of the sequence. Since this vector also contains a *Renilla* luciferase gene, the incorporation efficiency of the vector can be determined.

African green monkey renal cells (CV-1) were inoculated into a 24-well plate and cultured in DMEM (5% charcoal-treated fetal bovine serum) for one day. A reporter plasmid (pG5-Luc; Promega) containing the GAL4-binding sequence upstream of a firefly luciferase gene and the pBIND-PPARα LBD were simultaneously added to the plate (0.2 µg/well each) by use of a transfection reagent (Superfect transfection reagent QIAGEN). Thereafter, the culture medium was exchanged with DMEM (− fetal bovine serum) medium containing a test substance in an amount of 0.002% (w/v), followed by further culturing for one day. The test substance was each of the extracts prepared in Production Examples 1 and 2 and Comparative Production Examples 1 to 4. The same amount of a solvent (ethanol) was employed as a control. Wy14643 (obtained from BIOMOL (Plymouth Meeting DA)) (10 µM) was employed as a positive control.

After washing with PBS, the cells were lysed by means of Dual Luciferase Assay System (Promega). A substrate solution containing luciferin was added to the lysate, and each of firefly luciferase activity and *Renilla* luciferase activity was determined by means of a luminometer, PPARα-dependent gene transcriptional activity (luciferase activity) was defined as follows.

PPARα-dependent gene transcriptional activity (luciferase activity)=(firefly luciferase activity by pG5-Luc)/(*Renilla* luciferase activity by pBIND-PPARα LBD)

FIG. 1 shows the PPARα activation abilities of the respective test substances. The PPARα activation ability of each test substance is represented by a relative value with respect to the PPARα-dependent transcriptional activity of the control, which is taken as 1. The significant difference against the control group was tested by the Dunnett method.

According to FIG. 1, a 50% ethanol extract or hexane extract of the tempeh-fungus-fermented soybean product exhibits PPARα activation ability, and particularly, the hexane extract (i.e., hydrophobic solvent extract) exhibits high activation ability. In contrast, a solvent extract of soybean does not exhibit PPARα activation ability. These data indicate that fermentation of soybeans with the tempeh fungus is required for activation of PPARα.

Example 2

PPARδ Activation Test

A PPARδ activation test was carried out in a manner similar to that described in Example 1.

A PPARδ ligand binding site (NCBI RefSeq NM_011145, nt690-1595, SEQ ID NO: 2) was amplified, through PCR by use of Rat IEC-6 total RNA. The PCR amplified product was cloned into pCR Blunt (Invitrogen), and a DNA fragment was prepared through treatment with restriction enzymes (MluI, KpnI; Takara). The thus-prepared DNA fragment was inserted, into a multi-cloning site (MluI/KpnI) of pBIND vector (Invitrogen), to thereby produce pBIND-PPARδ LED.

In a manner similar to that described in Example 1, cells into which the aforementioned vector had been incorporated were cultured together with a test substance, and the luciferase activity of the test substance was determined. GW501516 (ALEXIS BIOCHEMICALS) (1 nM) was employed as a positive control. PPARδ-dependent gene transcriptional activity (luciferase activity) was defined as follows.

PPARδ-dependent gene transcriptional activity (luciferase activity)=(firefly luciferase activity by pG5-Luc)/(*Renilla* luciferase activity by pBIND-PPARδ LED)

Figure 2:
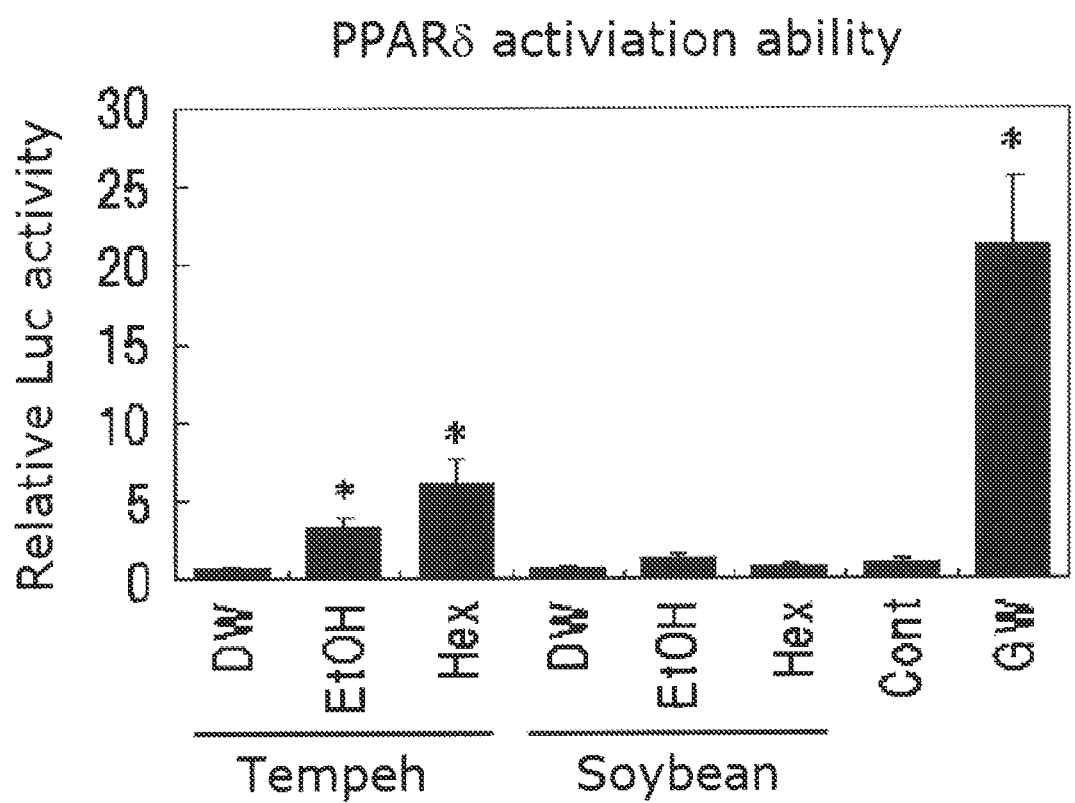
FIG. 2 is a graph showing PPARδ activation ability (wherein DW represents a water extract; EtOH represents a 50% ethanol extract; Hex represents a hexane extract; Cont represents a solvent control; GW represents GW501516; and * represents a significant difference (P<0.05) with respect to the solvent control).

FIG. 2 shows the PPARδ activation abilities of the respective test substances. The PPARδ activation ability of each test substance is represented by a relative value with respect to the PPARδ-dependent transcriptional activity of the control, which is taken as 1. The significant difference against the control group was tested by the Dunnett method.

According to FIG. 2, a 50% ethanol extract or hexane extract of the tempeh-fungus-fermented soybean product exhibits PPARδ activation ability, and particularly, the hexane extract (i.e., hydrophobic solvent extract) exhibits high activation ability.

Example 3

PPARγ Activation Test

A PPARγ activation test was carried out in a manner similar to that described in Example 1.

A PPARγ2 ligand binding site (NCBI RefSeq NM_015869, nt703-1606, SEQ ID NO: 3) was amplified through PCR by use of Human colon total RNA (Clontech). The PCR amplified product was cloned into pCR Blunt (Invitrogen), and a DNA fragment was prepared through treatment with restriction enzymes (MluI, KpnI; Takara). The thus-prepared DNA fragment was inserted into a multi-cloning site (MluI/KpnI) of pBIND vector (Invitrogen), to thereby produce pBIND-PPARγ LED.

In a manner similar to that described in Example 1, cells into which the aforementioned vector had been incorporated were cultured together with a test substance, and the luciferase activity of the test substance was determined. Pioglitazone (CAYMAN) (10 μM) was employed as a positive control. PPARγ-dependent gene transcriptional activity (luciferase activity) was defined as follows.

PPARγ-dependent gene transcriptional activity (luciferase activity)=(firefly luciferase activity by pG5-Luc)/(Renilla luciferase activity by pBIND-PPARγ LBD)

Figure 3:
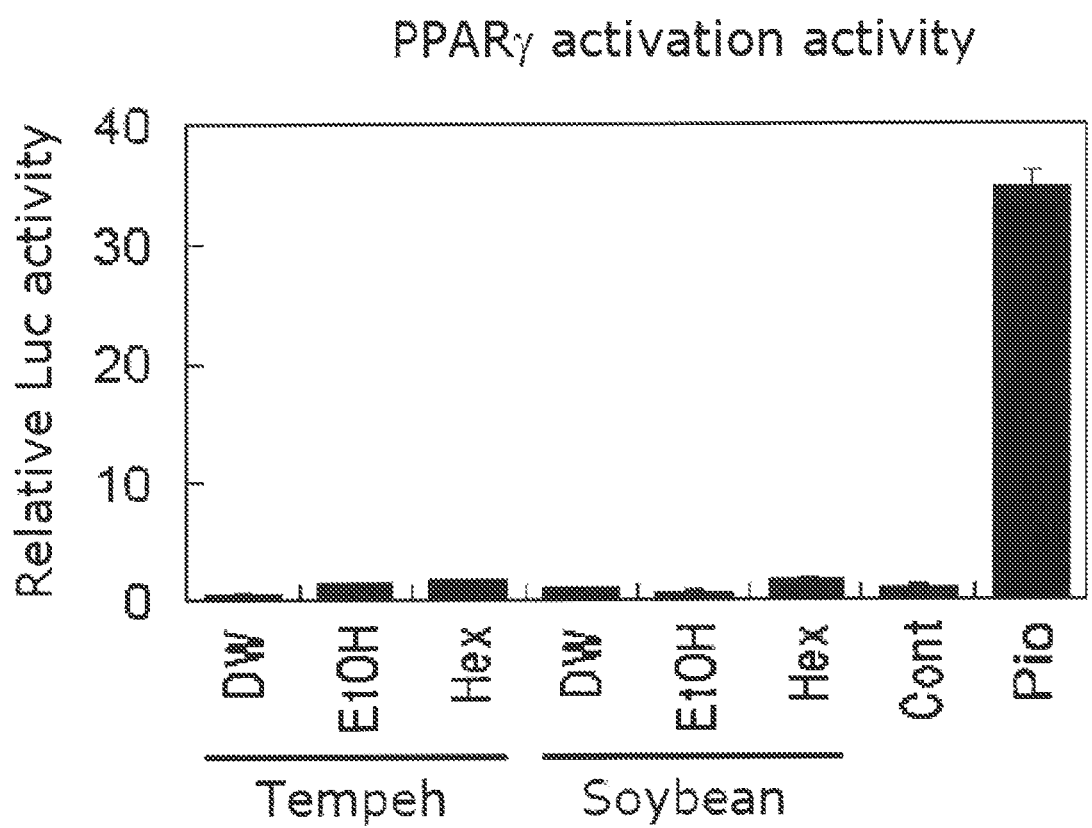
FIG. 3 is a graph showing PPARγ activation ability (wherein DW represents a water extract; EtOH represents a 50% ethanol extract; Hex represents a hexane extract; Cont represents a solvent control; and Pio represents pioglitazone).

FIG. 3 shows the PPARγ activation abilities of the respective test substances. The PPARγ activation ability of each test substance is represented by a relative value with respect to the PPARγ-dependent transcriptional activity of the control, which is taken as 1. The significant difference against the control group was tested by the Dunnett method.

According to FIG. 3, an organic solvent extract of the tempeh-fungus-fermented soybean product does not activate PPARγ.

As described above, the organic solvent extract of the tempeh-fungus-fermented soybean product exhibits a PPARα-activating effect and a PPARδ-activating effect, but does not exhibit a PPARγ-activating effect; i.e., the organic solvent extract exhibits high specificity to PPARα and PPARδ. That is, the organic solvent extract can be employed as an PPARα- or PPARδ-selective activator.

Since the organic solvent extract of the tempeh-fungus-fermented soybean product exhibits a PPARα or PPARδ-activating effect, as described above, the organic solvent extract is considered to be effective for activation of fatty acid metabolism, promotion of body fat burning, prevention and/or amelioration of obesity, prevention and/or amelioration of dyslipidemia, prevention and/or amelioration of fatty liver, improvement of physical endurance, prevention and/or amelioration of insulin resistance increase or diabetes, prevention and/or amelioration of arteriosclerosis, etc.

The invention claimed is:

1. A method for activating PPARα and/or PPARδ in a subject in need of improvement of physical endurance, the method comprising administering an organic solvent extract of a tempeh-fungus-fermented soybean product to the subject, wherein the organic solvent is (a) hexane (b) ethanol, or (c) a mixture of water and ethanol, and wherein the subject is administered 1 to 5,000 mg of the organic solvent extract per 60 kg body weight per day.

2. A method for improving physical endurance in a subject in need thereof, the method comprising administering an organic solvent extract of a tempeh-fungus-fermented soybean product to the subject, wherein the organic solvent is (a) hexane (b) ethanol, or (c) a mixture of water and ethanol, and wherein the subject is administered 1 to 5,000 mg of the organic solvent extract per 60 kg body weight per day.

3. The method according to claim 1, wherein the organic solvent is hexane.

4. The method according to claim 2, wherein the organic solvent is hexane.

* * * * *